US010286399B2

(12) United States Patent
Porter et al.

(10) Patent No.: US 10,286,399 B2
(45) Date of Patent: *May 14, 2019

(54) SYNTHESIS APPARATUS AND METHOD

(71) Applicant: Touchlight IP Limited, London (GB)

(72) Inventors: Neil Porter, London (GB); Paul James Rothwell, London (GB)

(73) Assignee: Touchlight IP Limited, London (GB)

( * ) Notice: Subject to any disclaimer, the term of this patent is extended or adjusted under 35 U.S.C. 154(b) by 280 days.

This patent is subject to a terminal disclaimer.

(21) Appl. No.: 14/771,125

(22) PCT Filed: Mar. 4, 2014

(86) PCT No.: PCT/GB2014/050634
§ 371 (c)(1),
(2) Date: Aug. 27, 2015

(87) PCT Pub. No.: WO2014/135859
PCT Pub. Date: Sep. 12, 2014

(65) Prior Publication Data
US 2016/0008815 A1    Jan. 14, 2016

(30) Foreign Application Priority Data

Mar. 5, 2013   (GB) .................................. 1303913.6

(51) Int. Cl.
*B01F 15/00*      (2006.01)
*B01L 7/00*       (2006.01)
(Continued)

(52) U.S. Cl.
CPC ..................... *B01L 7/52* (2013.01);
*B01F 5/10* (2013.01); *B01F 11/0005* (2013.01); *B01F 13/08* (2013.01); *B01F 13/1055* (2013.01); *B01F 15/00162* (2013.01); *B01F 15/00246* (2013.01); *B01F 15/00253* (2013.01); *B01F 15/065* (2013.01); *B01J 19/0033* (2013.01);
(Continued)

(58) Field of Classification Search
None
See application file for complete search history.

(56) References Cited

U.S. PATENT DOCUMENTS 5,637,469 A * 6/1997 Wilding .............. B01F 15/0264
                                                366/DIG. 3
7,772,010 B2    8/2010 Dugas et al.
(Continued)

FOREIGN PATENT DOCUMENTS

| EP | 1714695 A1 | 10/2006 |
|---|---|---|
| WO | 88/00347 A1 | 1/1988 |
| WO | 02/24317 A1 | 3/2002 |

OTHER PUBLICATIONS

PCT Search Report dated Jun. 23, 2014 of Patent Application No. PCT/GB2014/050634 filed Mar. 4, 2014.

*Primary Examiner* — Robert T. Crow
(74) *Attorney, Agent, or Firm* — Maine Cernota & Rardin

(57) ABSTRACT

Apparatus for biochemical synthesis having a reaction vessel, a temperature control device for the reaction vessel, a plurality of reservoirs for reaction components, and supply/withdrawal systems, e.g. reciprocating syringe pumps and switchable valves. Agitation of a reaction mixture is effected by withdrawing a part of the mixture from the reaction vessel and returning it thereto.

10 Claims, 4 Drawing Sheets

Figure 1:
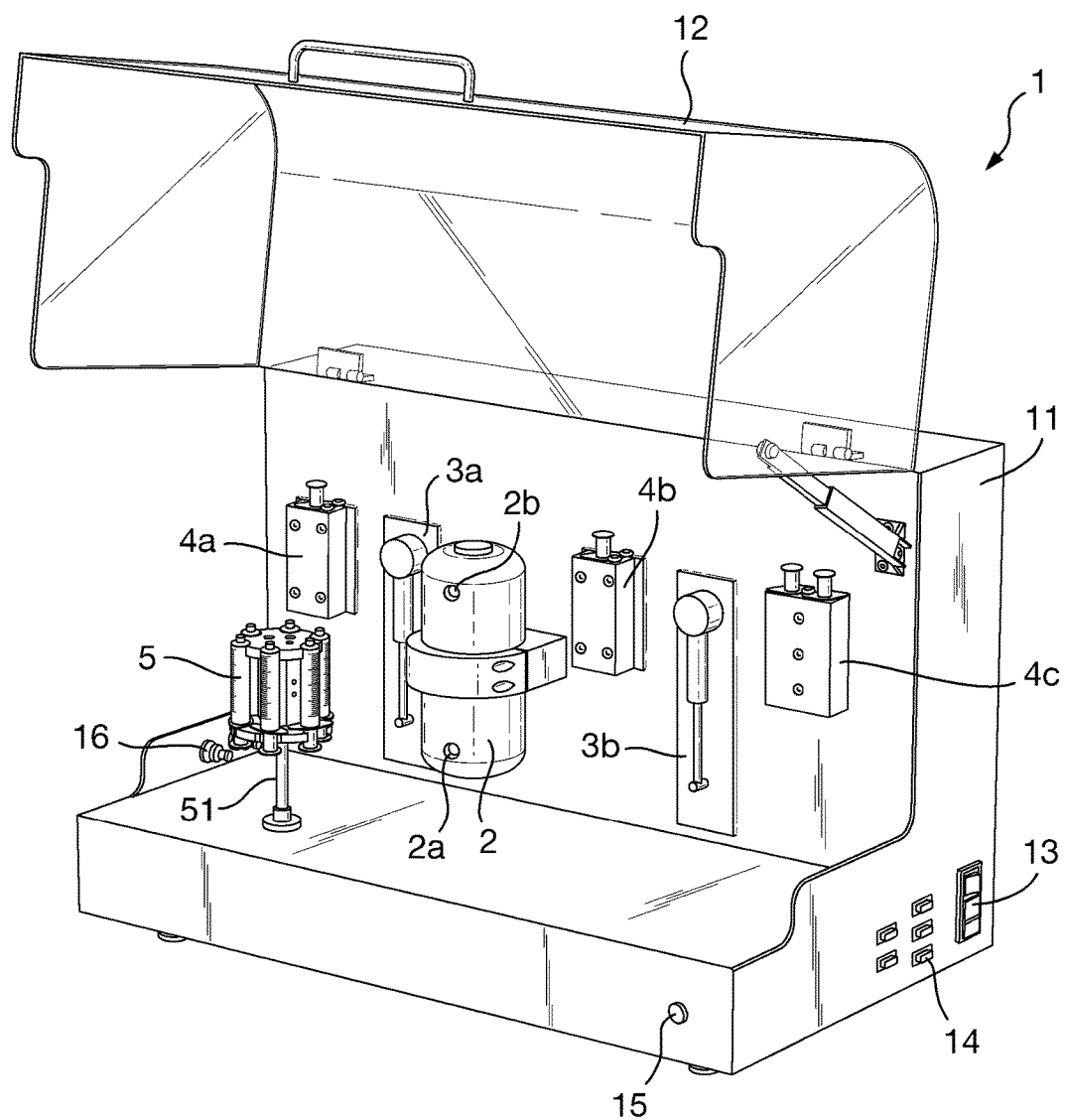

(51) Int. Cl.
*B01F 5/10* (2006.01)
*B01J 19/00* (2006.01)
*B01F 13/10* (2006.01)
*B01F 15/06* (2006.01)
*B01F 11/00* (2006.01)
*B01F 13/08* (2006.01)
*C12P 19/34* (2006.01)

(52) U.S. Cl.
CPC ........... *B01J 19/0046* (2013.01); *C12P 19/34* (2013.01); *B01J 2219/00099* (2013.01); *B01J 2219/00135* (2013.01); *B01J 2219/00137* (2013.01); *B01J 2219/00162* (2013.01); *B01J 2219/00202* (2013.01); *B01J 2219/00236* (2013.01); *B01J 2219/00286* (2013.01); *B01J 2219/00342* (2013.01); *B01J 2219/00409* (2013.01); *B01J 2219/00418* (2013.01); *B01J 2219/00477* (2013.01); *B01J 2219/00495* (2013.01); *B01J 2219/00698* (2013.01); *B01L 2300/0663* (2013.01); *B01L 2300/1822* (2013.01); *B01L 2300/1827* (2013.01); *B01L 2400/0475* (2013.01); *B01L 2400/082* (2013.01)

(56) References Cited

U.S. PATENT DOCUMENTS

| | | | |
|---|---|---|---|
| 2001/0010916 A1* | 8/2001 | Schleifer | B01J 19/0046 435/6.11 |
| 2005/0014246 A1* | 1/2005 | Kohara | G01N 33/54366 435/287.1 |
| 2005/0037517 A1* | 2/2005 | Anderson | G01N 30/24 436/173 |
| 2005/0042768 A1* | 2/2005 | Fredrick | B01J 19/0046 506/33 |
| 2005/0056713 A1* | 3/2005 | Tisone | B01D 19/0047 239/690 |
| 2006/0037644 A1* | 2/2006 | Nishikawa | G05D 7/0641 137/487.5 |
| 2006/0182664 A1* | 8/2006 | Peck | B01J 19/0046 422/400 |
| 2007/0117212 A1* | 5/2007 | Kautz | B01L 3/502784 436/137 |
| 2008/0104885 A1* | 5/2008 | Sinoncelli | B01F 5/0665 44/451 |
| 2012/0304776 A1* | 12/2012 | Novotny | B82Y 15/00 73/668 |

* cited by examiner

SYNTHESIS APPARATUS AND METHOD

RELATED APPLICATIONS

This application is a national phase application filed under 35 USC § 371 of PCT Application No. PCT/GB2014/050634 with an International filing date of Mar. 4, 2014, which claims priority to GB1303913.6, filed Mar. 5, 2013. Each of these applications is herein incorporated by reference in their entirety for all purposes.

The present invention relates to an apparatus for biochemical synthesis, in particular to synthesis of DNA, RNA, proteins and like molecules, as well as corresponding methods.

Amplification of DNA may be carried out through use of cell-based processes, such as by culture of bacteria propagating a DNA to be amplified in fermenters. Cell-free enzymatic processes for amplification of DNA from a starting template have also been described, including the polymerase chain reaction and strand-displacement reactions. WO 2010/086626 and WO 2012/017210 describe in vitro cell-free processes for formation of closed linear DNA by use of a DNA polymerase and a protelomerase.

In the past, amplification of DNA on a test scale has been performed using apparatus based on microtitre plates and robotically controlled pipettes to add reaction components as required. Such apparatus are suitable for manufacturing small quantities of DNA molecules for test purposes but do not provide sufficient quantities for other purposes. Large scale amplification and manufacture of specific proteins has mostly been carried out through cell-based processes. Such methods are effective for production of very large volumes of product but costly to set up.

There are also many apparatus available that are specifically adapted to amplify DNA samples using the thermocyclic method to effect the polymerase chain reaction (PCR). These apparatus are ideally suited to that reaction but are inflexible and cannot be adapted to perform other reactions. An example of such an apparatus is disclosed in U.S. Pat. No. 8,163,489.

There is therefore a need for an adaptable apparatus that can be used to carry out various biochemical reactions at significant scale.

According to the present invention, there is provided a synthesis apparatus comprising:
 a reaction vessel;
 a temperature control device for controlling the temperature of the reaction vessel;
 a plurality of reservoirs for holding reaction components;
 supply/withdrawal means selectively connectable to the reservoirs and the reaction vessel so as to supply controlled amounts of reaction components held in the reservoirs to the reaction vessel at desired times and to withdraw material from the reaction vessel; and
 control means for controlling the supply/withdrawal means to withdraw and return a part of the contents of the reaction vessel so as to agitate/mix the contents of the reaction vessel.

According to the present invention, there is provided a method of synthesis comprising:
 adding a plurality of reaction components to a reaction vessel to form a reaction mixture;
 withdrawing a part of the reaction mixture from the reaction vessel and returning the withdrawn part thereto in order to agitate the reaction mixture and ensure mixing thereof; and
 withdrawing reaction product from the reaction vessel at the end of the reaction.

Figure 2:
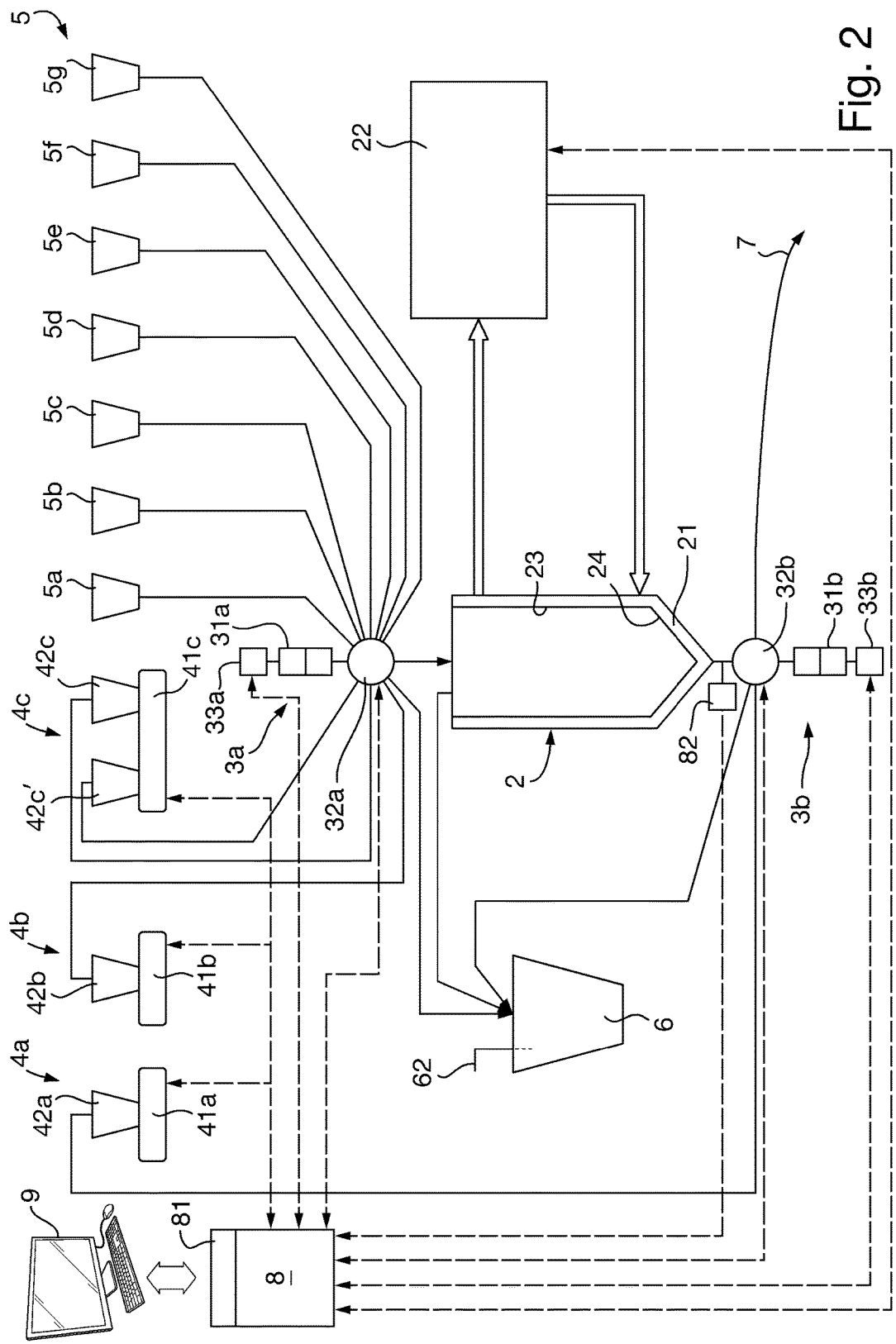
Figure 3:
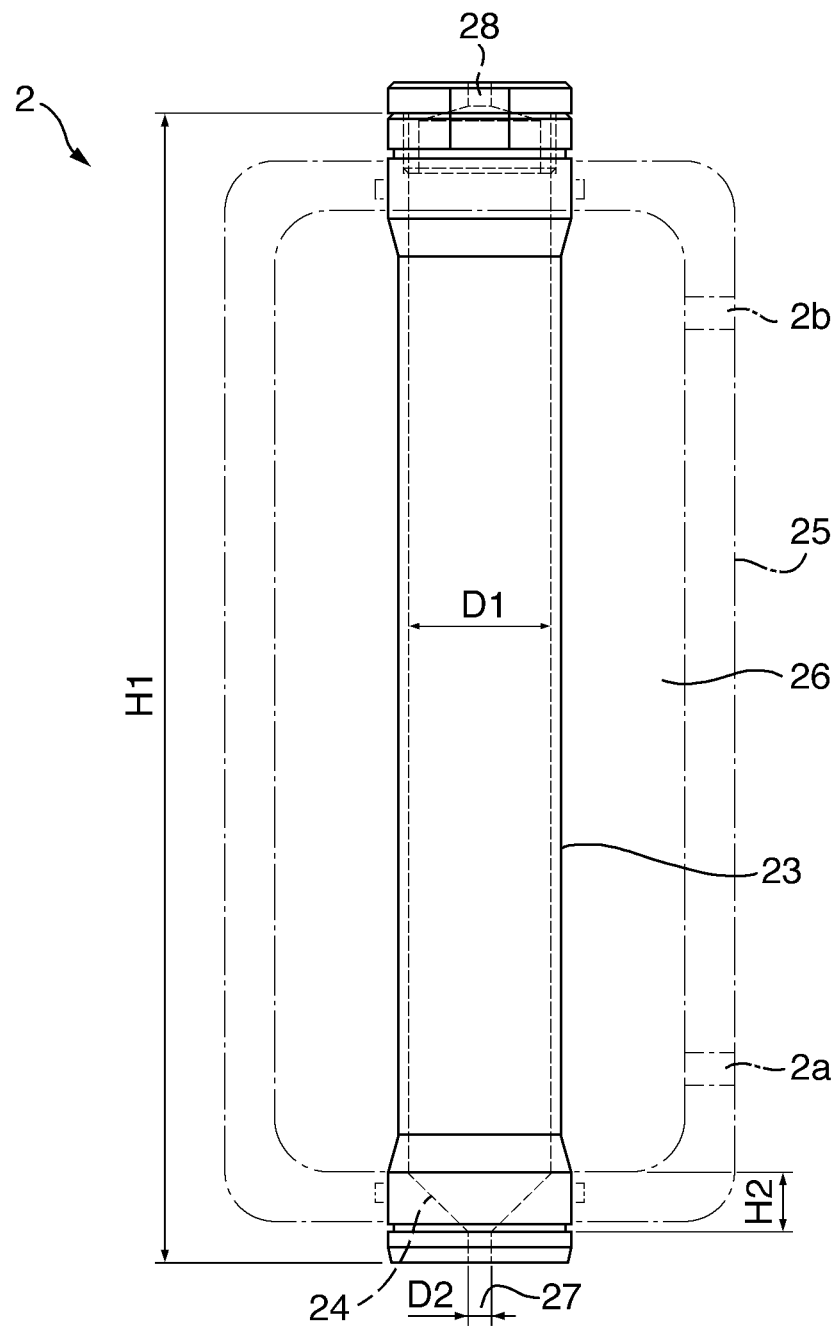
Figure 4:
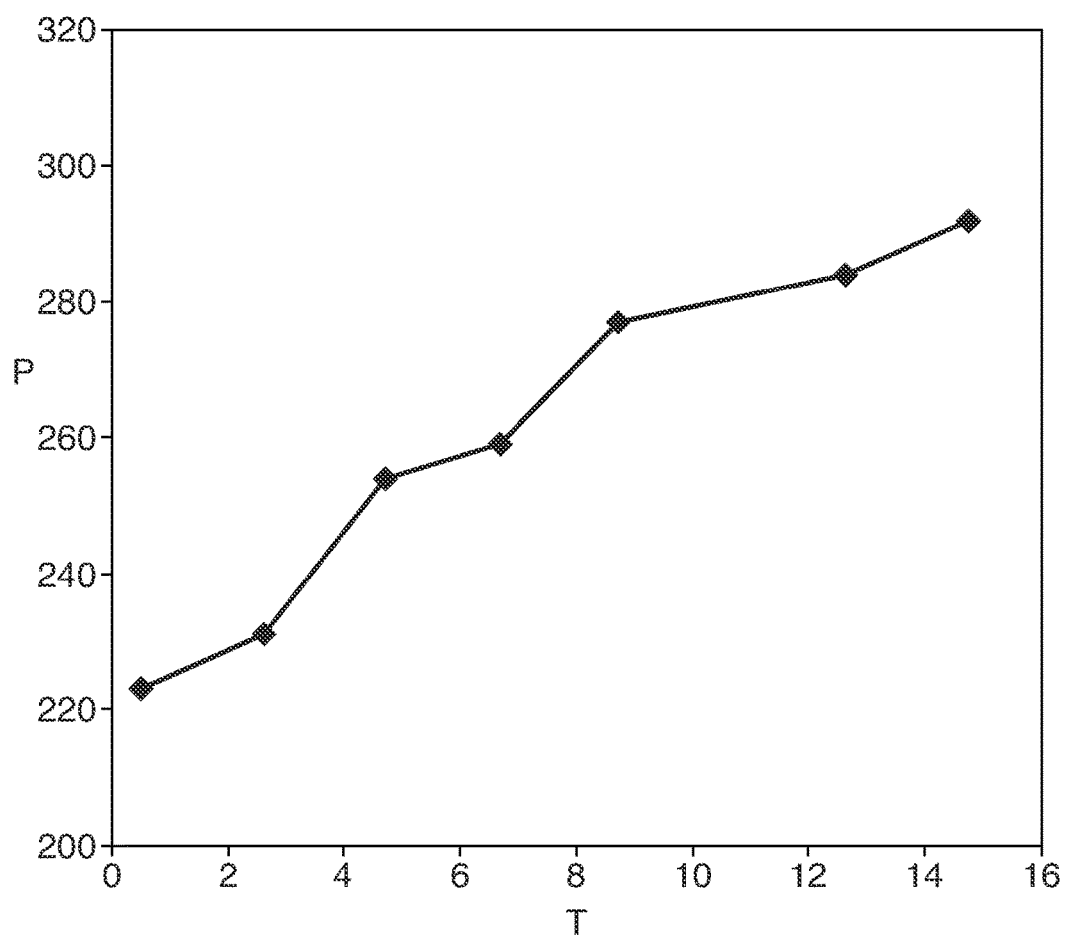

The present invention will be described further below with reference to exemplary embodiments and the accompanying drawings, in which:

FIG. 1 is a perspective view of a synthesis apparatus according to an embodiment of the invention;
FIG. 2 is a schematic diagram of the apparatus of FIG. 1;
FIG. 3 is a cross-sectional view of a reaction vessel of an embodiment of the invention; and
FIG. 4 is a graph of pressure differential vs time in an example process using the invention.

In the various drawings, like parts are indicated by like references.

A synthesis apparatus according to the present invention is capable of carrying out automatically desired reactions involving biochemical molecules such as DNA, RNA and proteins. Reactions are performed in a temperature-controlled reaction vessel to which various reaction components can be delivered in desired amounts, e.g. volumes, and to a desired schedule to effect the desired reaction(s).

In an embodiment, the temperature of the reaction vessel can be controlled accurately to follow a desired temperature profile in synchronism with the addition of reaction components and/or withdrawal of material.

In an embodiment, the reaction vessel is arranged and provided with means to enable the contents thereof to be agitated and/mixed as desired. In embodiment the reaction vessel is appropriately shaped so that withdrawal and return of a controlled amount of the reaction mixture serves to adequately mix the reaction mixture.

In an embodiment, the reaction vessel is desirably arranged so that it tapers towards its lowest point where an inlet/outlet support is provided. For example, the cross-sectional area of the reaction vessel monotonically reduces towards the lowest point of the reaction vessel. In an embodiment, the reaction vessel is provided with a main part having a constant cross-sectional area throughout its height. In an embodiment, the horizontal cross-section of the reaction vessel is substantially circular throughout its height.

In an embodiment, the aspect ratio of the reaction vessel, that is the ratio of the height of the reaction vessel to the width of the reaction vessel, is in the range of from 5:1 to 8:1, preferably in the range of from 6:1 to 7:1. In the case of a reaction vessel that is not circular in horizontal cross-section, the aspect ratio is determined with reference to the largest horizontal dimensions. The terms "horizontal" and "vertical" as used herein refer to the apparatus in its normal orientation for use.

In an embodiment, reaction components are stored and/or delivered to the reaction vessel at a controlled temperature. In an embodiment of the invention, the apparatus has a plurality of temperature-controlled reservoirs for reaction components. In an embodiment, the temperature controlled reservoirs are provided with a temperature control device to set a desired temperature for the contents of the reservoir. In an embodiment, the temperature control device comprises a Peltier heating/cooling device and/or a resistive heater.

In an embodiment of the present invention, supply of reaction components and withdrawal of reaction products and/or samples is effected by one or more reciprocating syringe pumps. In an embodiment of the invention, one or more multiway valves is provided to selectively connect the or each reciprocating syringe pump to an inlet/outlet port of the reaction vessel and/or a reservoir.

In an embodiment, reaction mixture can be withdrawn from the reaction vessel at the end of a reaction or as desired during a reaction, e.g. for sampling purposes.

In an embodiment, the apparatus can be operated in batch mode or continuous processing mode.

In an embodiment, the apparatus is a closed system to prevent the ingress of contaminants.

In an embodiment, at least one reservoir comprises a removable syringe, e.g. a polypropylene syringe. In an embodiment, at least one of the reciprocating syringe pumps comprises a removable syringe, e.g. a glass or polypropylene syringe. In an embodiment, glass syringes are silanised to prevent DNA material adhering to the syringes.

FIG. 1 is a perspective view of a synthesis apparatus 1 according to an embodiment of the present invention. For ease of understanding and to make the main components more visible, certain components and connecting conduits are omitted in this Figure. FIG. 2 is a schematic diagram of the same apparatus.

Synthesis apparatus 1 is constructed on a self-contained chassis 11 and provided with an openable front cover 12 to allow access to the main components. The front cover 12 is desirably made of a transparent material but may be tinted to protect the reaction components from excessive light levels. It also serves to limit ingress of contaminants. The apparatus is provided with externally accessible power switch and power input 13, e.g. on a side of the apparatus. In addition there are input/output ports 14 to allow the apparatus to communicate with and/or be controlled by a general purpose computer executing laboratory automation software such as, for example, Labview™ supplied by National Instruments Corporation of Texas, USA. An operation indicator light 15 is provided at a position to be visible from the front of the apparatus and indicates whether or not the apparatus is in operation.

The central component of the synthesis apparatus is a jacketed reaction vessel 2 having a volume greater than 30 ml. In an embodiment, the volume of the reaction vessel is greater than 50 ml. In an embodiment the volume of the reaction vessel is about 75 or 120 ml. In an embodiment the volume of the reaction vessel is less than 300 ml. In an embodiment the volume of the reaction vessel is less than 200 ml. In an embodiment the volume of the reaction vessel is less than 150 ml. The volume of the reaction vessel can be selected in accordance with the intended use of the apparatus and the amount of product that is intended to be made in a batch, or the rate of production in a continuous process. Clearly, the size of the reaction vessel sets an upper limit on the amount of product that can be produced in a batch In an embodiment the aspect ratio of the reaction vessel is no greater than 8:1. In an embodiment the aspect ratio is no greater than 7:1. If the reaction vessel is too tall, it becomes harder to effect thorough mixing of the contents by withdrawal and return of reaction mixture. In an embodiment the aspect ratio is no less than 5:1. In an embodiment the aspect ratio is no less than 6:1. If the reaction vessel is too wide, it becomes more difficult to ensure an even temperature throughout, especially with smaller reaction volumes. Agitation of the mixture can assist in obtaining the desired temperature throughout the mixture, especially if the reaction mixture is heated to 95° C. Reaction vessels with aspect ratios within the above limits are adaptable to different quantities of reaction components.

A reaction vessel 2 usable in an embodiment of the invention is shown in cross-section in FIG. 3. The reaction vessel 2 comprises an inner vessel 23 surrounded by a jacket 25. Temperature control fluid is circulated though the space 26 between inner vessel 23 and jacket 25 in order to control the temperature of the contents of the inner vessel 23. Lower port 27 and upper port 28 are provided to connect the inner vessel to selection valves 32b, 32a respectively.

In an embodiment of the invention, the inner vessel 23 has a main part which has the form of a cylinder of diameter D1, e.g. in the range of 20 to 50 mm, preferably 25 to 35 mm, and a tapering part 24 connecting the cylindrical part to the lower port 27. The overall height H1 of the inner vessel is, in an embodiment, in the range of from 150 mm to 300 mm, desirably 200 mm to 250 mm. The height of the tapering part 24 is, in an embodiment, in the range of from 5 to 20 mm, preferably 10 to 15 mm. The angle of the side walls of the tapering part is in the range of from 30 to 60° relative to the axis of the inner vessel, preferably about 45°. The diameter D2 of the lower port 27 is in the range of from 5 to 10 mm.

In an embodiment of the invention, the reaction vessel has a non-constant cross-section, for example having a downwards taper throughout its height or a central bulge.

The temperature of the reaction vessel is controlled by a flow of temperature control fluid through the outer jacket to the reaction vessel. The temperature control fluid is supplied by inlet 2a and removed from outlet 2b by a recirculating temperature control device 22. The recirculating temperature control device controls the temperature of the temperature control fluid by heating and/or cooling the fluid. The reaction vessel can be maintained at a constant temperature, e.g. in spite of the occurrence of endothermic or exothermic reactions, or may be controlled to follow a desired temperature profile. The temperature control fluid may be water or oil. In an embodiment, the temperature control fluid is supplied via ports 16 provided on the chassis of the apparatus. A suitable recirculating temperature control device is the Presto A30 Temperature Control System manufactured by Julabo USA, Inc. of Pennsylvania, USA. In an embodiment of the invention, the recirculating temperature control device 22 comprises ohmic heaters and/or Peltier devices. In an embodiment, the temperature of the reaction vessel is controllable to a temperature with the range of from 4° C. to 95° C. with a precision of 0.01° C.

This embodiment of the present invention is provided with temperature-controlled reservoirs 4a-4c for reaction components to be used in the synthesis reaction. The reaction components are held in syringes 42a-42c, e.g. disposable polypropylene syringes, which are mounted in temperature control devices 41a-41c. The temperature control devices in this embodiment comprise blocks of conductive material, e.g. aluminium, having bores to closely receive the syringes 42a-42c. A thermally conductive paste can be provided if desired to increase thermal conductivity between the block and the syringes. Heating/cooling devices, e.g. ohmic heaters or Peltier devices, are attached to the thermally conductive blocks in order to control the temperature thereof and hence of the reaction components stored in the reservoirs 42a-42c.

Temperature control devices 41a-41c can be used either to heat or to cool the stored reaction components. Some reaction components are desirably held at a low temperature, e.g. about 4° C., in order to prevent degradation thereof. Primers can be stored at an elevated temperature so as to prevent and/or reduce primer diming. The reservoirs can also be heated to denature and anneal templates and primers prior to addition to the reaction vessel. As with the main temperature control of the reaction vessel, the temperature controlled reservoirs can be maintained at a constant temperature or follow a desired temperature profile, e.g. to heat a reaction component just before addition to the reaction vessel. In an embodiment the temperatures of the temperature-controlled reservoirs are independently controllable within a range of from 4° C. to 95° C. with a precision of 0.01° C.

In an embodiment, one or more in-line heaters (not shown) are provided to raise the temperature, e.g. to 95° C., of a reaction component such as a primer before addition to the reaction vessel. The heater, or one of the heaters if there are a plurality, is provided on the conduit between a reservoir 4a-c, 5a-g and selection valve 32c and/or between selection valve 32a and reaction vessel 2.

In this embodiment, one of the temperature controlled reservoirs 4c comprises two reservoir syringes 42c and 42c' in thermal contact with a single temperature control block 41c. This is useful where two reaction components need to be maintained at the same temperature or where a larger volume of a single reaction component is required for a desired reaction.

The apparatus also comprises a plurality of further reservoirs 5a-5g that are not provided with temperature controlling devices. In this embodiment there are seven such reservoirs, in other embodiments more or fewer are provided. The further reservoirs 5a-5g can also comprise syringes, e.g. glass or polypropylene syringes, that can be removed and disposed of when empty. The use of syringes is advantageous as the volume of the reservoir automatically reduces as reaction components are withdrawn. A similar effect can be achieved with collapsible bags or tubes. If a rigid container is used, it is desirable that a filter is provided in any vent to atmosphere in order to prevent ingress of contaminants.

Conveniently, a rotary stand 51 is provided to mount reservoirs 5. If a reaction component is required in large quantities, the apparatus can be provided with ports to connect to an external reservoir. Desirably, the apparatus is laid out so as to minimise the lengths of conduit required to connect the reservoirs to the selection valves. In an embodiment, the conduits are detachable from the reservoirs and then can be attached to a manifold which is connected to a supply of cleaning fluid or water for rinsing. In this way the entire apparatus can be cleaned flushed in situ, i.e. without being dismantled.

In an embodiment, reservoirs 4a-c and 5a-g have a capacity of from 3 to 10 ml, e.g. about 5 ml. One or more larger reservoirs can be provided, e.g. for buffer solutions, with a capacity of from 10 to 500 ml, e.g. about 250 ml.

Supply of a reaction component to the reaction vessel is effected by a reciprocating syringe pump 3a. This pump is referred to as the supply pump. This comprises a syringe 31a, e.g. a glass or polypropylene syringe, driven by a solenoid 33a and connected to a controllable selection valve 32a to selectively connect the syringe 31a to each of the reservoirs and the reaction vessel. To add a controlled amount of a reaction component to the reaction vessel, the selection valve 32a is first used to connect the pump syringe to the relevant reservoir then the solenoid is actuated to draw into the syringe the relevant volume of the reaction component. Next, the selection valve 32a is used to connect the syringe 31a to the reaction vessel 2 and the solenoid reversed to drive the syringe contents out into the reaction vessel. With this arrangement, it is possible to quickly add quantities of desired reaction components sequentially to the reaction vessel without requiring multiple syringe pumps and multiple inlets to the reaction vessel. However, if it is desirable to add multiple reaction components simultaneously to the reaction vessel it is possible to provide multiple supply pumps 3a. This can also be desirable if it is necessary to keep certain reaction components absolutely separate prior to their addition to the reaction vessel.

In this embodiment, a second reciprocating syringe pump 3b is used to agitate the contents of the reaction vessel as well as to remove reaction mixture or product either at the end of the reaction or for sampling purposes during a reaction process. This pump is referred to as the withdrawal pump and comprises a syringe 31b driven by a solenoid 33b. The second syringe pump 3b is connected to an outlet at the bottom of the reaction vessel via a second selection valve 32b. To agitate the contents of the reaction vessel, the second selection valve 32b is used to connect the syringe 31b to the reaction vessel whilst an amount of the reaction mixture is withdrawn from the reaction vessel and then returned thereto. The amount of the reaction mixture that is withdrawn and the rate at which it is returned can be controlled in order to control the degree of agitation that is effected. Such agitation can be effected continuously through the course of a reaction, periodically or at specific times relating to the addition of reaction components.

In an embodiment, second reciprocating syringe pump 3b is also connected to reservoir 4a and can be used to supply the reaction component stored in that reservoir to the reaction vessel 2.

A pressure sensor 82 is provided on a short spur connected to the conduit between reaction vessel 2 and selection valve 32b or between selection valve 32b and withdrawal pump 3b. During the withdrawal and return of material from or to the reaction vessel 2, the pressure measured by the sensor 82 is indicative of the viscosity of the mixture being transferred: the higher the pressure, the higher the viscosity. In particular, the amplitude of pressure variations during cyclic withdrawal and return of material is indicative of the viscosity of the reaction mixture. The exact relationship between pressure and viscosity is dependent on various factors including the rate of withdrawal or return of material, the diameter of the conduits used and the geometry of the reaction vessel. This relationship can be determined theoretically or by calibration. In an embodiment, the exact relationship is not necessary and the signals from pressure sensor 82 can simply be used to detect changes in the reaction mixture without knowing its exact viscosity. In a reaction where the viscosity increases due to product formation, the signal from the pressure sensor can be used to control the reaction. By activating the pump to deliver one or more appropriate reagents from one or more of the reservoirs at an appropriate rate or in an appropriate quantity based on the pressure signal, it is possible to increase product yield. In other cases, the pressure signal may indicate completion of the reaction or a stage in the reaction and so be used to trigger harvesting of the product or addition of components for a next stage.

In an embodiment of the invention, a signal from the pressure sensor 82 is used to control the rate of withdrawal and/or return of mixture to the reaction vessel to ensure that that DNA material in the mixture is not damaged by shear forces. In an embodiment, the rate of withdrawal and/or return of mixture is controlled to ensure that a pressure limit is not exceeded. The pressure limit can be viscosity dependent.

The present inventor has determined that agitation by removal and return of reaction mixture is particularly efficacious when used with a reaction vessel of a size, shape and aspect ratio as described above. This method of agitation is also effective for a wide range of volumes of reaction mixture. This setup also has advantages in that it does not require any components, such as baffles, inside the reaction vessel that might be difficult to clean.

In an embodiment of the invention alternative means for agitating the reaction mixture are provided, e.g. magnetic stirring devices within the reaction vessel and/or an agitator for shaking the whole reaction vessel.

To remove material e.g. reaction product from the reaction vessel, the withdrawal pump 3b is first connected to the reaction vessel by the second selection valve 32b and the solenoid operated to withdraw the piston of the syringe so as to withdraw material from the reaction vessel 2. The withdrawal pump is then connected to an exit port 7 by the second selection pump and the solenoid 33b activated to eject the collected material through the exit port 7.

Exit port 7 can be connected to, for example, a container for reaction product, a sample container, a measurement device or any other apparatus. It is also possible for a sample that has been removed for measurement purposes to be returned to the reaction vessel after the measurement.

In an embodiment of the invention the withdrawal pump 3b has a larger capacity than the supply pump 3a so that, for example, the entire reaction vessel can be emptied in a single pumping operation. Such a large capacity for the withdrawal pump 3b is also desirable to assist in cleaning the apparatus by flushing large volumes of cleaning solution and/or deionised water through the entire system. To this end, the apparatus can be provided with additional large reservoirs to hold sufficient quantities of cleaning solution and deionised water.

In an embodiment of the invention, a single pump is used to supply reaction components, to agitate the reaction mixture and to withdraw reaction mixture and/or product.

In an embodiment of the invention, the supply pump 3a and/or withdrawal pump 3b comprises another form of pump, e.g. a peristaltic pump.

The apparatus also comprises a waste vessel 6 which is connected to the atmosphere via a vent 62 which may be provided with a one-way valve. Waste vessel 6 is connected to the upper part of reaction vessel 2 so as to provide a vent therefore and prevent a build up of pressure in reaction vessel 2. Conduits are also provided to connect waste vessel 6 with selection valves 32a and 32b so as to allow dumping of product from the reaction vessel and any unused and undesired reaction components. The waste vessel can also be used to receive cleaning and rinsing fluids during in-situ cleaning and rinsing as well as small amounts of reaction components from priming of the conduits to enable exact delivery of desired amounts to the reaction vessel.

In an embodiment, waste vessel 6 can be omitted. In this case it is desirable to provide a safety valve to reaction vessel 2 and to provide connections from selection valves 32a, 32b to an external drain.

Operation of the apparatus is controlled by a controller 8 which is electrically connected to the temperature control devices 41a-c, to selection syringes 32a-b, to solenoids 33a-b, to temperature control device 22 and to pressure sensor 82 so as to control those components of the apparatus. Controller 8 also comprises an interface 81 allowing connection to an external computer 9 for overall control of the process to be carried out.

In an embodiment, the controller 8 is pre-programmed to perform specific commonly used routines such as priming, sampling, harvesting, rinsing and cleaning. In an embodiment, controller 8 simply passes commands from the external computer 9 to the different components of the apparatus. The routines mentioned can be performed under the control of an external computer or manually.

In an embodiment, priming the apparatus comprises drawing reaction components from each of the reservoirs to be used so that the conduits between the reservoirs and the selection valves are filled with the respective reaction component. This is desirable to increase accuracy in the amounts of reaction components delivered to the reaction vessel and reduces possibilities for contamination. In an embodiment, sampling the reaction mixture comprises removing a predetermined quantity of the reaction component to an external vessel or sensor during the course of a reaction. Return of the sample to the reaction vessel is possible in some cases. In an embodiment, harvesting comprises withdrawing some or all of the reaction product at the end of a batch process or at an appropriate time in a continuous process. In an embodiment rinsing comprises rinsing used conduits and reservoirs with pure water. In an embodiment, cleaning the apparatus comprises rinsing conduits and reservoirs with a cleaning solution.

In a method of the invention, a plurality of reaction components is added to a reaction vessel to form a reaction mixture. A part of the reaction mixture is withdrawn from the reaction vessel and returned thereto in order to agitate the reaction mixture and ensure mixing thereof. At the end of the reaction, reaction product is withdrawn from the reaction vessel. In an embodiment, the reaction mixture is withdrawn from a port provided at a lower part of the reaction vessel, preferably at the lowest point of the reaction vessel. In an embodiment, the part of the reaction mixture that is removed amounts to 50% or less of the whole reaction mixture, desirably 40% or less, preferably 30% or less. In an embodiment, the part of the reaction mixture that is removed amounts to 5% or more of the whole reaction mixture, desirably 10% or more, preferably 20% or more.

EXAMPLE

An example of a method of DNA synthesis using an apparatus according to an embodiment of the invention will now be described.

First the apparatus was cleaned and decontaminated. Tubes were disconnected from the 10 reagent reservoirs (42a, 42b, 42c', 42c, 5a to 5g) and reconnected via Luer fittings to a 10 position manifold fed from a 120 ml reservoir containing 10% sodium hypochlorite solution. Similarly, a 60 ml reservoir of 10% sodium hypochlorite solution was attached to exit port 7 from selection valve 32b. By controlling the positions of the selection valves 32a and 32b and the actions of solenoids 33a and 33b on the 5 ml glass syringes 31a and 31b respectively, the whole system including the reaction vessel 2 itself was completely filled with sodium hypochlorite solution with no dead spaces. A minimum of 5 ml of solution was drawn through each tube. The reaction vessel (120 ml capacity) was heated to 50° C. by control action on thermocirculator 22 and the system maintained in this state for a period of 30 minutes. This procedure ensured that all contaminating DNA within all the feed tubes and the reaction vessel itself was completely destroyed.

Similarly, by using an appropriate program to control the selection valves and solenoids described above, the whole system was emptied of sodium hypochlorite solution by dispensing it into the waste vessel 6. Repeating above the process 5 times after replacing the sodium hypochlorite solution in the reservoirs with deionised water ensured the complete removal of any residual sodium hypochlorite from the whole system making it ready for use.

The tubes were then disconnected from the manifold reconnected to the 10 reagent reservoirs comprising sterile disposable polypropylene syringes with Luer lock fittings (5 ml to 20 ml capacity). Where indicated below, these syringes contained individual reaction components in a minimum volume of 2 ml. Otherwise they were left empty with the plungers fully depressed. Reservoir 5d consisted of two 60 ml syringes in parallel to give a total capacity of 120 ml of deionised water. In syringes containing reagents, air in each syringe barrel was expelled, after filling, by manually depressing the plunger until liquid just escaped from the syringe outlet. During this procedure, the syringe outlet was kept vertically above the syringe plunger to permit the expulsion of all the air in the barrel.

tinuous with the syringe activated for 10 minutes at intervals of approximately 2 hours at a withdrawal/dispense rate of 70 ml/min.

The pressure change in the tubing between reaction vessel 2 and syringe 31b was measured by a vacuum and pressure sensor 82 (Model ZSE30-01-26, SMC Corporation, Tokyo, Japan). This sensor measures pressure differences of −101 to +101 kPa (−1000 to +1000 mbar) and was connected via a T-piece using a short section of ⅛ inch diameter PTFE tubing. The output signal from the sensor (0-5V) was monitored using a Pico Technology USB TC-O8 data logger (Pico Technology, Cambridge, UK). The data logger was

TABLE 1

| Addition order | Reservoir | Reservoir Temp °C. | Reagent | Concentration | Volume dispensed | Concentration in reactor |
|---|---|---|---|---|---|---|
| 1 | 5a | Room Temp | Circular DNA template DB-Cal092 | 1 mg/ml | 400 µl | 10 µg/ml |
| 2 | 5b | Room Temp | Oligonucleotide primer NO-7 | 1 mM | 400 µl | 10 µM |
| 3 | 5c | Room Temp | KOH | 1M | 400 µl | 10 mM |
| 4 | 5f | Room Temp | 10x Buffer 300 mM Tris-HCl, pH 7.5 300 mM KCl 75 mM $MgCl_2$ 50 mM $(NH_4)_2SO_4$ 20 mM DTT | | 4 ml | 30 mM Tris-HCl, pH 7.5 30 mM KCl 7.5 mM $MgCl_2$ 5 mM $(NH_4)_2SO_4$ 2 mM DTT |
| 5 | 42c | 4.0 | Phi 29 DNA polymerase | 10,000 units/ml | 800 µl | 200 units/ml |
| 6 | 42c' | 4.0 | Pyrophosphatase | 200 units/ml | 80 µl | 0.4 units/ml |
| 7 | 5e | Room Temp | dNTPs | 100 mM | 800 µl | 2 mM |
| 8 | 5d | Room Temp | $H_2O$ | | 33.12 ml | |

The enzyme reagents, Phi29 DNA polymerase and pyrophosphatase, in reservoirs 42c and 42c' respectively, were maintained under stable conditions at 4° C. by temperature control device 41c. All other reagents were maintained at room temperature.

To achieve accurate dispensing of reagents into reaction vessel 2, the tubes between the reagent reservoirs and the selection valves 32a and 32b were primed by sequentially withdrawing very small amounts of the reagents and dispensing to waste vessel 6.

To denature the DNA template and bind the oligonucleotide primer, the reagents from reservoirs 5a, 5b and 5c were dispensed via selection valve 32a (by the action of solenoid 33a on syringe 31a) into a closed empty 5 ml syringe (reservoir 42b). The temperature of this reservoir was controlled by temperature control device 41b. Control action on 41b was used to raise its temperature to 95° C. for 3 minutes and then cool to 30° C. The combined reaction components in reservoir 42b were then dispensed into reaction vessel 2 via selection valve 32a. The remaining 5 reaction components were sequentially dispensed via selection valve 32a in the order show in Table 1 such that the final volume in reaction vessel 2 was 40 ml. The temperature of reaction vessel 2 was set at 30° C. by control action on thermocirculator 22. The reaction components were not exposed to surface temperatures greater than 2° C. above the set point.

Mixing of the reaction components was achieved by control action on the solenoid 33b and subsequently on the movement of mixing syringe 31b. The syringe action was controlled to withdraw from and return to the reaction vessel 2, 5 ml of reaction components. The mixing was disconprogrammed to record the mV output from the sensor at 400 millisecond intervals and the output was plotted in real time during the course of the reaction.

The reciprocating action of the mixing syringe resulted in a graphical output showing peaks of high and low pressure. With all other variables fixed such as syringe speed, tubing material, internal diameter and length and selection valve size and geometry any change in peak height could only be due to a change in viscosity of the reaction components. Very small pressure changes that might be attributed to environmental temperature and pressure fluctuations were not compensated for in pressure difference calculations.

During the process, the action of the Φ29 DNA polymerase on the circular DNA template, DB-Cal092 produces long linear concatameric repeats of the template that may extend to 70 kilobases or more, the reaction finishing when one or more of the reaction components is exhausted. Long single strands of DNA are produced first which then act as a template for the polymerase to produce the complementary strand. The product composition at the end of the reaction may include both single and double stranded concatameric DNA that increase the viscosity.

Measurement of this change in viscosity is reflected in the increase in pressure differential recorded by the sensor as shown in FIG. 4, which plots pressure difference P in mbar vs. time T in hours. It can be seen that over the course of about 14 hours, the pressure difference P increased from about 225 mbar to about 290 mbar. The increase was monotonic, but not quite linear, with the rate of increase fluctuating about the average.

The increase in the differential pressure observed during the course of the reaction can be accounted for by the increase in solution viscosity due to the production of DNA. Confirmation of this increase was confirmed from visual examination of removed samples; these showed a gradual increase in their ability to retain trapped air bubbles as the reaction proceeded.

The invention has been described with reference to exemplary embodiments only and is not to be construed as limited thereto but includes variations and modifications falling within the scope of the appended claims.

The invention claimed is:

1. A synthesis apparatus comprising:
    a reaction vessel having a first lower port and a second upper port;
    a temperature control device for controlling the temperature of the reaction vessel;
    a plurality of reservoirs for holding reaction components;
    a plurality of conduits, each of the plurality of conduits connecting the second upper port of the reaction vessel with a respective one of the plurality of reservoirs;
    a pressure sensor configured to measure pressure of content in a conduit external to said reaction vessel that connects an agitation device-to the reaction vessel;
    a supply pump configured to selectively supply controlled amounts of reaction components held in the plurality of reservoirs to the reaction vessel at desired times; and
    a controller configured to control the supply pump and the agitation device;
    wherein the agitation device is configured to selectively withdraw an amount of content from the reaction vessel through the first lower port thereof and selectively return the withdrawn content to the reaction vessel through the first lower port thereof; and
    wherein the pressure sensor is configured to send a signal to the controller, the signal being indicative of a pressure in the conduit connecting the agitation device to the reaction vessel that can be used to infer the viscosity of the mixed reaction components, and
    wherein the controller is configured to control the rate of withdrawal from or return of reactants to the reaction vessel, using the agitation device, in response to a change in the signal received from the pressure sensor, thereby ensuring that a predefined pressure limit is not exceeded and that the mixed reaction components are not damaged by high shear forces.

2. The synthesis apparatus according to claim 1 wherein the reaction vessel is arranged so that it tapers towards its lowest point and has an inlet/outlet port at the lowest point.

3. The synthesis apparatus according to claim 1 wherein the aspect ratio of the reaction vessel is in the range of from 5:1 to 8:1.

4. The synthesis apparatus according to claim 1 wherein the temperature control device is arranged to control the temperature of the reaction vessel to follow a desired temperature profile upon the addition of reaction components and/or withdrawal of material.

5. The synthesis apparatus according to claim 1 further comprising a reservoir temperature control device arranged to control the temperature of a reaction component held in the plurality of reservoirs.

6. The synthesis apparatus according to claim 1 wherein the temperature control device comprises a thermocirculator, a Peltier heating/cooling device and/or a resistive heater.

7. The synthesis apparatus according to claim 1 wherein the supply pump and the agitation device comprise reciprocating syringe pumps.

8. The synthesis apparatus according to claim 1 wherein the supply pump comprises a multi-way valve arranged to selectively connect the supply pump to the first port of the reaction vessel or a reservoir.

9. The synthesis apparatus according to claim 1 wherein at least one reservoir comprises a glass or polypropylene removable syringe.

10. The synthesis apparatus according to claim 1 wherein the agitation device comprises a multi-way valve arranged to selectively connect the agitation device to the second port of the reaction vessel or a reservoir.

* * * * *